United States Patent [19]

Goldberg et al.

[11] Patent Number: 5,387,613
[45] Date of Patent: Feb. 7, 1995

[54] TREATMENT OF TACHYARRHYTHMIAS OF SUPRAVENTRICULAR ORIGIN

[75] Inventors: Arthur H. Goldberg, Montclair; Leonard Lachman, Fort Salonga, both of N.Y.

[73] Assignee: RiboGene, Inc., Hayward, Calif.

[21] Appl. No.: 95,349

[22] Filed: Jul. 23, 1993

[51] Int. Cl.6 .................................. A61K 31/135
[52] U.S. Cl. .................................. 514/652; 514/821
[58] Field of Search .................................. 514/652, 821

[56] References Cited

U.S. PATENT DOCUMENTS 3,337,628  8/1967  Crowther et al. .................. 514/652
4,394,390  7/1983  Hussain et al. ..................... 514/652

OTHER PUBLICATIONS

CA(100)13:96447h.

Primary Examiner—Marianne M. Cintins
Assistant Examiner—K. Weddington
Attorney, Agent, or Firm—Pennie & Edmonds

[57] ABSTRACT

This invention relates to the treatment of tachyarrhythmias of supraventricular origin. This condition may safely be treated by nasal administration of a composition comprising propranolol dissolved in a pharmaceutically acceptable, aqueous-based carrier. A total dose of up to 20 mg of propranolol may be administered at one time.

14 Claims, No Drawings

TREATMENT OF TACHYARRHYTHMIAS OF SUPRAVENTRICULAR ORIGIN

FIELD OF THE INVENTION

The present invention relates to a novel method for administering propranolol to treat supraventricular tachyarrhythmias.

BACKGROUND ART

Numerous β-adrenergic blocking agents are known for the treatment of various forms of cardiac arrhythmias. It is additionally common to treat some, but not all types of supraventricular tachyarrhythmias, with a β-blocker such as propranolol.

Where β-adrenergic blocking agents are appropriate, substantial oral doses have conventionally been administered chronically in order to control these arrhythmias. A total dose of at least 80 mg per day and up to 1000 mg per day of propranolol, for example, has been recommended to control tachyarrhythmias. A part of this total dosage is usually taken every 4 to 8 hours. The primary objective of such therapy has been prophylactic—i.e. to maintain a reasonable heart rate as opposed to converting the arrhythmia.

Recently, another approach has been followed for treatment of certain tachyarrhythmias. This approach is for acute treatment. It involves a carefully monitored, intravenous titration of a β-adrenergic blocking agent. The need for great care derives from the danger of a β-blockade from injected propranolol. A β-blocking agent which is not significantly diffused in the bloodstream—i.e. a bolus—can drastically lower blood pressure and is capable of causing cardiac standstill on reaching the heart. As a result, this approach has been followed only under direct physician control, normally in a hospital setting.

This relatively new, acute treatment involves the sequential administration of a series of small increments of dilute β-blocker. The administration is performed very slowly; for example, on a metered basis of no more than 1 mg of propranolol per minute. Each separate administration is normally followed by a hiatus of one or two minutes before the next. This technique also utilizes a comparatively minor total dose of β-adrenergic blocking agent, usually less than 10 mg of propranolol. Together, these factors minimize the bolus effect of the drug.

The nasal administration of β-adrenergic blocking agents has also been suggested as a general means for the treatment of cardiac problems. This technique, which involves substitution of nasal for conventional oral or intravenous administration, is described in U.S. Pat. Nos. 4,428,883 and 4,394,390 (the disclosures of which are incorporated hereby by reference). It specifically references treatment of arrhythmias. These patents, however, do not describe any specific procedure or objective.

SUMMARY OF THE INVENTION

It is an object of the present invention to provide a novel method for the administration of propranolol in order to treat tachyarrhythmias of a supraventricular origin.

It is a further object of this invention to provide a safe method of treating such tachyarrhythmias; one capable of self-administration and which may be performed immediately and virtually anywhere.

It is also an object of this invention to utilize propranolol for treating such tachyarrhythmias on an essentially acute basis in order to minimize the side effects and potentially adverse consequences of such a drug.

These and other objects are achieved in accordance with the present invention which comprises nasally administering a composition comprising propranolol dissolved in a pharmaceutically acceptable aqueous-based carrier, a total dose of up to 20 mg of propranolol being administered immediately to reduce heart rate.

In accordance with the prior art prophylactic procedure, it is customary to provide sufficient blocking agents to maintain an effective concentration in the blood stream over an extended time. In contrast, the present invention permits a direct and less intrusive use of β-adrenergic blocking agent. Propranolol may be administered only as needed and in reduced dosage amount as compared to a prophylactic procedure. As a consequence, occurrences of adverse drug reaction, overdosage and/or discontinuance reaction are markedly reduced.

As compared to the prior art procedure of acute administration, the present invention is even more surprising. This method utilizes higher concentrations and greater dosages of propranolol administered more quickly than an intravenous administration. Notwithstanding these differences, the present invention is far safer.

DETAILED DESCRIPTION OF THE INVENTION

This invention provides an improved method for the treatment of limited types of cardiac arrhythmias. More specifically, this invention is directed towards those forms of tacharrhythmias which are of a supraventricular origin. These include atrial fibrillation, atrial flutter, paroxysmal supraventricular tachycardia, persistent sinus tachycardia, persistent atrial extrasystoles and tachycardia due to thyrotoxicosis.

In most instances, these forms of tachyarrhythmia are initiated by a disorder of impulse formation and/or propagation caused by atrial premature contractions, usually following a myocardial infraction. These particular forms of tachyarrhythmia are believed to result from disturbances at the atrioventricular node, as opposed to other conduction systems of the heart.

The present invention involves the nasal administration of an immediate dose up to about 20 mg of propranolol for the treatment of supraventricular tachyarrhythmia. Preferably the dose is from 5 to 15 mg of propranolol. By "immediate", it is meant that all the drug is administered at essentially one time, instead of slowly or incrementally over a prolonged period.

Surprisingly, undesirable effects have not been encountered incident this nasal means of administration. Due to various unique factors of the nasal induction of propranolol, this method does not require medically trained personnel or special medical facilities. It has been discovered to be so safe that it can be self-administered by the patient The term "propranolol", as utilized herein, encompasses any pharmaceutically acceptable form of this compound which is water-soluble. Preferably, the propranolol is present as a free base, ester or a salt, such as propranolol hydrochloride. In these forms, the propranolol is delivered with maximum speed into the blood stream and to the heart of a patient.

The amount of propranolol in the present compositions is normally substantial. Desirably these compositions contain at least 20 mg of propranolol per ml, more preferably from 30 to 70 mg per ml of solution. Notwithstanding the prompt impact of this highly concentrated dosage form, however, no bolus effect is encountered.

Administration of the propranolol is performed in a pharmaceutically-acceptable, aqueous-based nasal carrier. The nature of these carriers is particularly important to the successful treatment of supraventricular tachyarrhythmia. The propranolol must be solubilized in water for the reasons already pointed out.

The carrier may have any conventional form. Aqueous liquids, ointments and gels may all be used. For other examples, reference is made of the text entitled "REMINGTON'S PHARMACEUTICAL SCIENCES", 14th edition, 1970 (which is incorporated herein by reference). Preferred carriers comprise at least 80%, more preferably 90 to 99%, water by total weight. In another preferred form, the carrier is sprayable. This further facilitates its administration.

The nasal compositions of the present invention may contain various additional or optional components to ensure optimum therapeutic effect. These include one or more buffers, preferably selected to ensure a pH of between about 4 and 8. A preservative, such as an antibactericide, is also desirable. A cytoprotective agent may be employed to reduce the tendency of propranolol to irritate the cells within the nose. Further, minor amounts (usually less than 10% by weight) of organic solvents such as glycol may be included to ensure solubilization of the propranolol.

Administration of the present nasal compositions may be performed by any means which coats the nostril(s) of the patient suffering from supraventricular tachyarrhythmia. Thus it can be administered as nose drops, spray or any other means known in the art. The composition is preferably provided in a metered pump aerosol. In this manner, precise dosage amounts which are normally from about 0.5 to 0.1 ml per spray can be self-administered.

Soon after administration, the effect of the present compositions becomes evident. Most apparent is the reduction of heart rate. During tachyarrhythmia, the heart rate is well over 100 beats per minute and commonly ranges between about 125 to 350 beats per minute in humans. After administration, this rate will slow until it stabilizes at a more normal rate, desirably between about 60 to 90 beats per minute.

An example of the present nasal compositions and their use is set forth below. It is to be understood, however, that this example is only illustrative. It should not be construed as limiting this invention, as there are numerous modifications which will be apparent to those of ordinary skill in the art.

EXAMPLE

A study was performed involving 24 patients having confirmed diagnoses of tachyarrhythmia of a supraventricular origin. These patients were divided into two groups in order to compare the results of intravenous and nasal administration of propanol using a double dummy design.

The two different groups of patients experiencing heart rates of about 160 beats per minute were treated as follows:

Group A:

These patients were infused intravenously with a 1 mg/ml aqueous solution of propranolol hydrochloride on a three minute cycle of 1 ml over the first minute, followed by two minutes of waiting. The cycle was repeated up to seven times, administration being terminated when the patient's heart rate reached 80 beats per minute.

In addition to the foregoing, a single placebo spray of 0.1 ml of water was injected into each nostril of the patient at the onset of the intravenous administration of active drug.

Group B:

Each patient received a 0.1 ml spray of an aqueous solution of propranolol hydrochloride in each nostril. The concentration of the solution was 50 mg propranolol per ml.

This nasal administration was followed by a placebo intravenous infusion performed in the same manner as described for Group A.

During the study, 20% of the patients of Group A suffered one or more moderately severe, cardiovascular events. These were primarily short-lived hypotension or bradycardia attributed to the propranolol. Even though the nasal administration involved much higher and more concentrated dosage levels, no such events occurred in patients of Group B. This emphasized the greater safety of nasal administration of propranolol for the acute treatment of tachyarrhythmia.

During and after the onset of dosing, the heart rates of both groups of patients were monitored. This data was then graphed against time for a six hour period. The heart rates of patients in both groups dropped significantly and reached approximately 80 to 90 beats per minute within less than two hours. Despite the differences in timing and total propranolol dosage, there was no statistical deviation between the resultant plots for intravenous and nasal forms of administration. Thus both the simple procedure used for nasal administration and that for intravenous titration proved equally effective in reducing the rate of heart beat.

While the present invention has been described in terms of certain preferred embodiments, various modifications including substitutions and omissions may be made in them without departing from its spirit. Accordingly, it is intended that the scope of the invention be limited solely in accordance with the following claims.

What is claimed is:

1. A method for the acute treatment of tachyarrhythmia of supraventricular origin comprising nasally administering a composition comprising propranolol dissolved in a pharmaceutically acceptable aqueous-based carrier to a patient experiencing a tachyarrhythmia of supraventricular origin which causes the heart to beat at a heart rate of above about 100 beats per minute, said composition administered immediately at a total dose of up to 20 mg. of propranolol to significantly reduce the heart rate.

2. The method of claim 1, wherein the composition contains at least 20 mg propranolol per ml of solution.

3. The method of claim 1, wherein the total dose of propranolol is from 5 to 15 mg.

4. The method of claim 3, wherein the composition comprises at least 80% of water by weight.

5. The method of claim 4, wherein the composition is self-administered.

6. The method of claim 5, wherein the propranolol is in the form of propranolol hydrochloride.

7. The method of claim 6, wherein the composition is administered as a spray.

8. The method of claim 5, wherein the tachyarrhythmia treated is atrial fibrillation.

9. The method of claim 5, wherein the tachyarrhythmia treated is atrial flutter.

10. The method of claim 5, wherein the tachyarrhythmia treated is paroxysmal supraventricular tachycardia.

11. The method of claim 5, wherein the tachyarrhythmia treated is persistent sinus tachycardia.

12. The method of claim 5, wherein the tachyarrhythmia treated is due to thyrotoxicosis.

13. The method of claim 5, wherein the tachyarrhythmia is due to persistent atrial extrasystoles.

14. The method of claim 1 which further comprises administering the composition to a patient experiencing a tachyarrhythmia of supraventricular origin which causes a heart rate of about 125–350 beats per minute, said composition administered immediately so as to reduce the heart rate to about 60 to 90 beats per minute within about two hours.

* * * * *